United States Patent
Lloyd et al.

(10) Patent No.: US 6,322,574 B1
(45) Date of Patent: Nov. 27, 2001

(54) DISPOSABLE LANCET

(75) Inventors: William A. Lloyd, Montréal; Martin Lancing, Pierrefonds, both of (CA)

(73) Assignee: Medical Plastic Devices M.P.D. Inc., Pointe Clarie (CA)

( * ) Notice: Subject to any disclaimer, the term of this patent is extended or adjusted under 35 U.S.C. 154(b) by 0 days.

(21) Appl. No.: 09/431,189

(22) Filed: Nov. 1, 1999

(51) Int. Cl.[7] ..................................... A61B 17/32

(52) U.S. Cl. ......................................... 606/181; 606/182

(58) Field of Search ................................ 606/181, 182, 606/183; 600/583

(56) References Cited

U.S. PATENT DOCUMENTS

| | | |
|---|---|---|
| 236,084 * | 12/1880 | Reinhold et al. . |
| 931,791 * | 8/1909 | Niergarth . |
| 4,064,871 * | 12/1977 | Reno . |
| 4,157,086 * | 6/1979 | Maiorano et al. . |
| 4,203,446 | 5/1980 | Hofert et al. . |
| 4,230,118 | 10/1980 | Holman et al. . |
| 4,375,815 | 3/1983 | Burns . |
| 4,388,925 | 6/1983 | Burns . |
| 4,414,975 | 11/1983 | Ryder et al. . |
| 4,442,836 | 4/1984 | Meinecke et al. . |
| 4,449,529 | 5/1984 | Burns et al. . |
| 4,452,243 | 6/1984 | Leopoldi et al. . |
| 4,503,856 | 3/1985 | Cornell et al. . |
| 4,527,561 | 7/1985 | Burns . |
| 4,535,769 | 8/1985 | Burns . |
| 4,553,541 | 11/1985 | Burns . |
| 4,577,630 | 3/1986 | Nitzsche et al. . |
| 4,580,565 | 4/1986 | Cornell et al. . |
| 4,616,649 | 10/1986 | Burns . |
| 4,624,253 | 11/1986 | Burns . |
| 4,676,244 | 6/1987 | Enstrom . |
| 4,677,979 | 7/1987 | Burns . |
| 4,715,374 | 12/1987 | Maggio . |
| 4,735,203 | 4/1988 | Ryder et al. . |
| 4,738,261 | 4/1988 | Enstrom . |
| 4,817,603 | 4/1989 | Turner et al. . |
| 4,844,095 | 7/1989 | Chiodo et al. . |
| 4,856,515 | 8/1989 | Turner et al. . |
| 4,889,117 | 12/1989 | Stevens . |
| 4,892,097 | 1/1990 | Ranalletta et al. . |
| 4,920,977 | 5/1990 | Haynes . |
| 4,990,154 | 2/1991 | Brown et al. . |
| 5,074,872 | 12/1991 | Brown et al. . |
| 5,100,427 | 3/1992 | Crossman et al. . |
| 5,105,823 | 4/1992 | Blum . |
| 5,152,775 | 10/1992 | Ruppert . |
| 5,196,025 | 3/1993 | Ranalletta et al. . |
| 5,201,324 * | 4/1993 | Swierczek . |
| 5,304,192 | 4/1994 | Crouse . |
| 5,314,441 | 5/1994 | Cusack et al. . |
| 5,318,583 | 6/1994 | Rabenau et al. . |

(List continued on next page.)

Primary Examiner—Michael H. Thaler
(74) Attorney, Agent, or Firm—Ryan Krombolz & Manion, S.C.

(57) ABSTRACT

A disposable lancet for puncturing skin is disclosed herein. The lancet comprises a T-shaped housing, a reciprocally movable elongated body that embeds a puncturing needle and a leaf spring to bias the elongated body towards a safe neutral position, where the puncturing device is retracted in the housing. The elongated body is generally cross-shaped and is guided by projections in the housing that define a cross-shaped passage. The leaf spring is located in the handle portion of the T-shaped housing and cooperates with the elongated body via a slit provided in the elongated body. The lancet is operated by pressing a portion of the elongated body that extends from the handle portion of the housing at one end. The lancet is then in a puncturing position, where the puncturing needle extends out of the housing at the distal end thereof. The elongated body returns to the safe neutral position when the force applied to the elongated body is no longer sufficient to overcome the biasing action of the leaf spring.

20 Claims, 3 Drawing Sheets

U.S. PATENT DOCUMENTS

| | | |
|---|---|---|
| 5,318,584 | 6/1994 | Lange et al. . |
| 5,324,302 | 6/1994 | Crouse . |
| 5,324,303 | 6/1994 | Strong et al. . |
| 5,366,469 | 11/1994 | Steg et al. . |
| 5,366,470 | 11/1994 | Ramel . |
| 5,385,571 | 1/1995 | Morita . |
| 5,395,387 | 3/1995 | Burns . |
| 5,397,334 | 3/1995 | Schenk et al. . |
| 5,421,347 | 6/1995 | Enstrom . |
| 5,423,847 | 6/1995 | Strong et al. . |
| 5,439,473 | 8/1995 | Jorgensen . |
| 5,454,828 | 10/1995 | Schraga . |
| 5,456,875 | 10/1995 | Lambert . |
| 5,464,418 | 11/1995 | Schraga . |
| 5,476,474 | 12/1995 | Davis et al. . |
| 5,487,748 | 1/1996 | Marshall et al. . |
| 5,514,152 | 5/1996 | Smith . |
| 5,527,334 | 6/1996 | Kanner et al. . |
| 5,529,581 | 6/1996 | Cusack . |
| 5,540,709 | 7/1996 | Ramel . |
| 5,545,174 | 8/1996 | Schenk et al. . |
| 5,554,166 | 9/1996 | Lange et al. . |
| 5,569,286 | 10/1996 | Peckham et al. . |
| 5,571,132 | 11/1996 | Mawhirt et al. . |
| 5,584,846 | 12/1996 | Mawhirt et al. . |
| 5,624,458 | 4/1997 | Lipscher . |
| 5,628,764 | 5/1997 | Schraga . |
| 5,628,765 | 5/1997 | Morita . |
| 5,630,828 | 5/1997 | Mawhirt et al. . |
| 5,643,306 | 7/1997 | Schraga . |
| 5,645,555 | 7/1997 | Davis et al. . |
| 5,662,672 | 9/1997 | Pambianchi et al. . |
| 5,680,872 | 10/1997 | Sesekura et al. . |
| 5,707,384 | 1/1998 | Kim . |
| 5,730,753 | 3/1998 | Morita . |
| 5,733,300 | 3/1998 | Pambianchi et al. . |
| 5,746,761 | 5/1998 | Turchin . |
| 5,755,733 | 5/1998 | Morita . |

\* cited by examiner

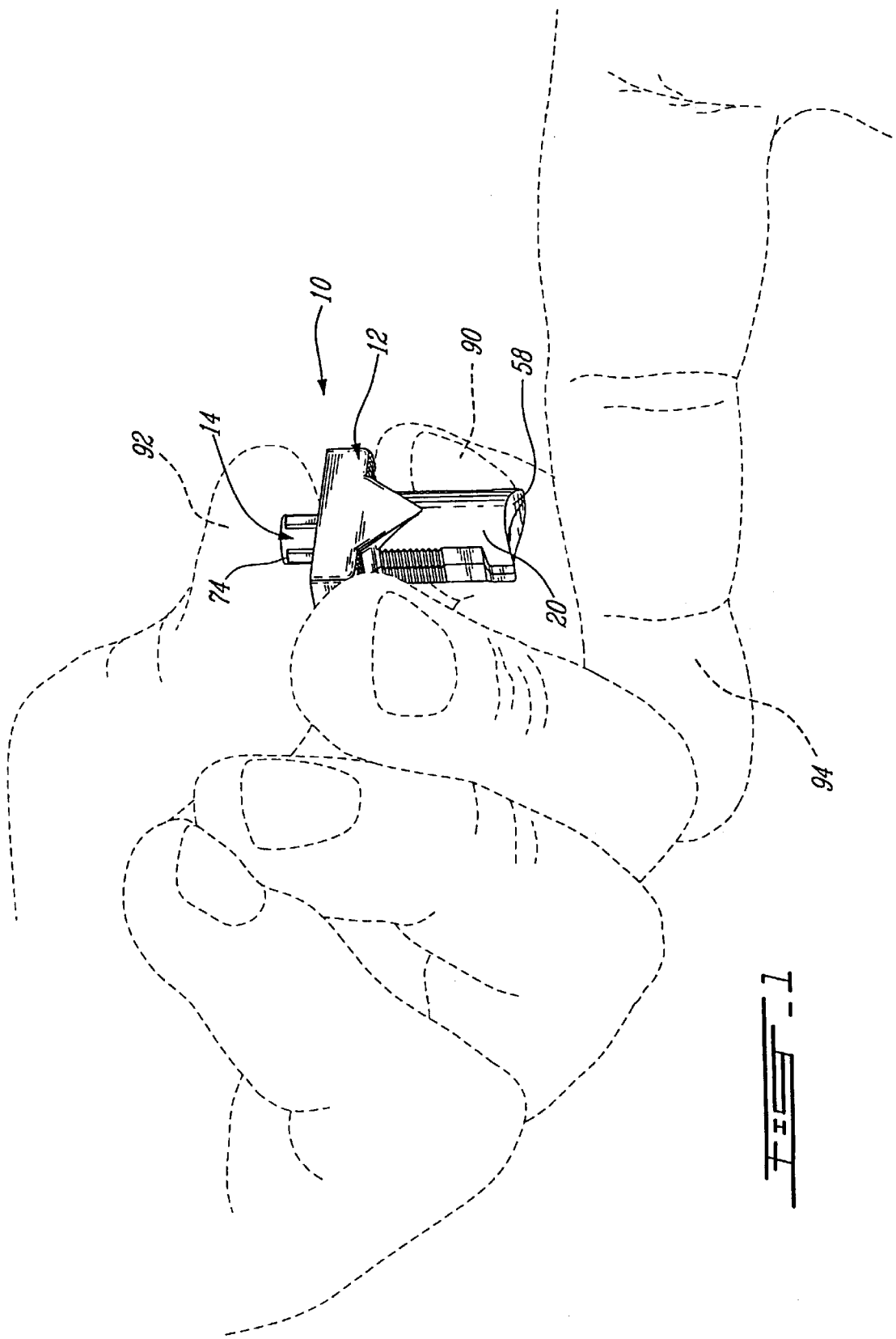

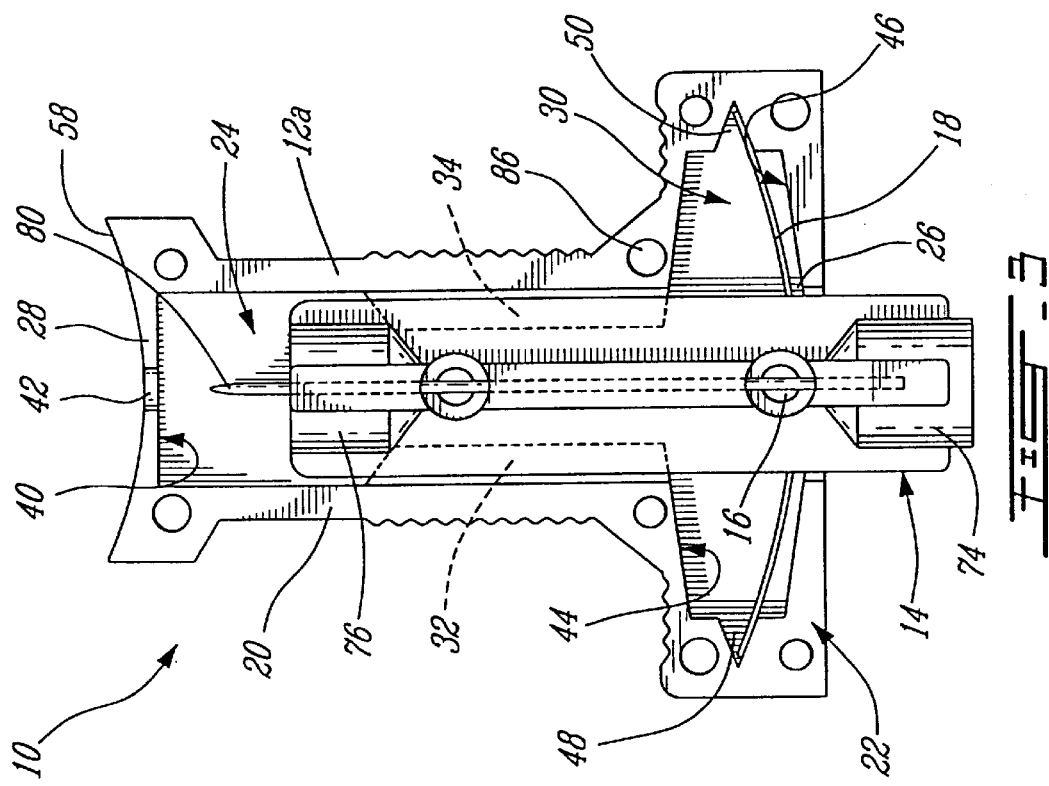
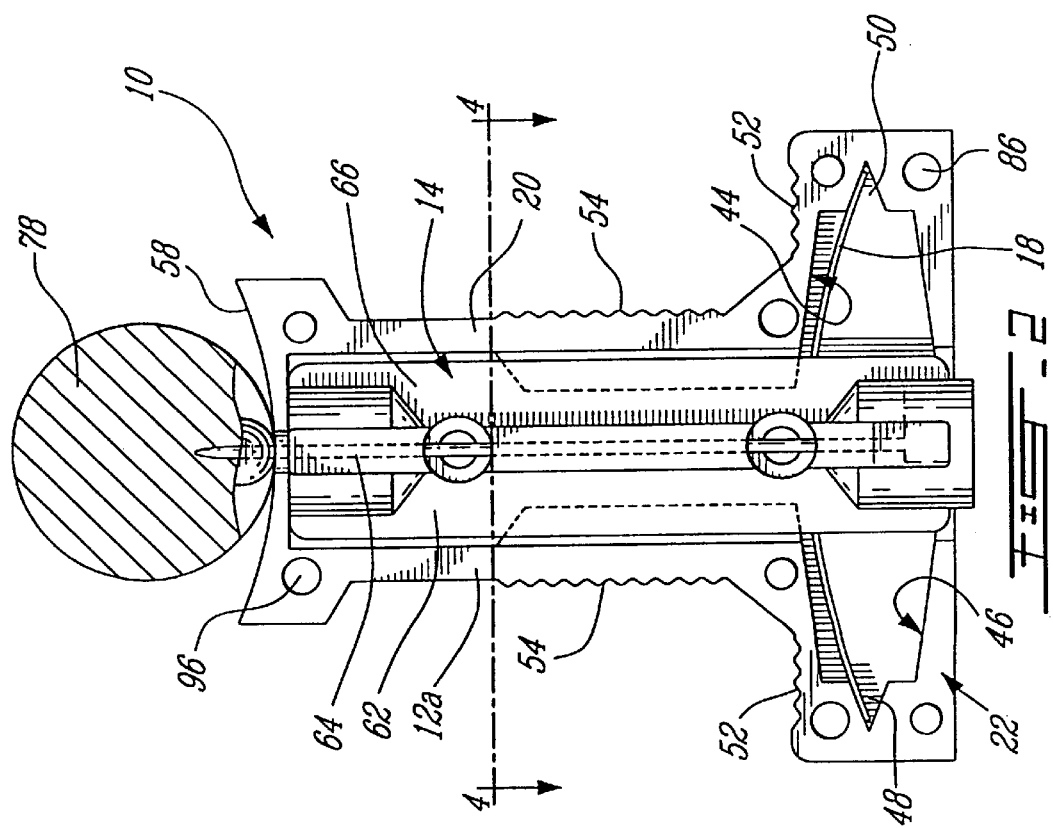

DISPOSABLE LANCET

FIELD OF THE INVENTION

The present invention relates to a lancet device for puncturing the skin.

BACKGROUND OF THE INVENTION

Lancets are conventionally used to puncture skin for providing blood samples. They are used primarily by people suffering from diabetes since they need to regularly analyse their blood sugar content. Lancets conventionally include a puncturing device, in the form of a small blade or a needle, that is advantageously mounted to a body.

Most lancets include a housing and a mechanism so configured as to retract the body in the housing when the lancet is not in use. This feature is advantageous since it prevents accidental use of the lancet.

A distinction can be made between two types of lancets. The first type usually includes a pen like housing that allows the removal of both the body and the needle so as to replace them after use. The internal mechanism of such lancet must be configured to allow the body to safely retract in the pen like housing but also to allow the body to be removed therefrom after use, which increases the complexity of the internal mechanism.

The second type of lancets (hereinafter referred to as disposable lancets) are relatively simpler to manufacture even though they may be provided with a retractable mechanism.

An example of such disposable lancet is described in the U.S. Pat. No. 4,624,253, naming James A. Burns as the inventor and issued on Nov. 25, 1986. Burns discloses a lancet that includes a generally cylindrical housing provided with a handle portion, a puncturing device holder having a puncturing blade mounted thereto and a helicoidal compression spring. The puncturing device holder is so mounted in the housing as to be reciprocally movable therein while being biased towards a neutral position by the helicoidal spring.

A drawback of Burns' lancet is that the assembly of a spring around the puncturing device holder can be tedious thus increasing the costs involved in the manufacturing of such a lancet. Also, since the puncturing blade is not embedded in a cap before use, Burn's lancet requires additional packaging to insure that the blade remains sterilized.

Another disposable lancet is described in the U.S. Pat. No. 5,529,581, issued on Jun. 25, 1996 and naming Robert Cusack as the inventor. Cusack's lancet includes a spring member, in the form of a curved invertible structure, that biases a small puncturing blade towards a safe position when not in use. A drawback of Cusack's lancet is that the retractable mechanism does not allow the blade to be embedded in a cap thus requiring additional packaging to insure that the blade remains sterilized.

OBJECTS OF THE INVENTION

An object of the present invention is therefore to provide an improved disposable lancet free of the above-mentioned drawbacks.

SUMMARY OF THE INVENTION

More specifically, in accordance with the present invention, there is provided a lancet for puncturing skin comprising:

a housing defining a passage having a proximal end and a distal end;

an elongated body having a proximal end and a distal end; the elongated body being so mounted in the passage as to reciprocate between a safe neutral position and a puncturing position;

a puncturing device provided at the distal end of the elongated body; the puncturing device extending from the distal end of the passage when the elongated body is in the puncturing position; and a leaf spring so mounted to both the elongated body and the housing as to bias the elongated body towards the safe neutral position; wherein the elongated body is moved from the safe neutral position to the puncturing position when a force is so applied thereto as to overcome the biasing action of the leaf spring.

Other objects, advantages and features of the present invention will become more apparent upon reading of the following non restrictive description of preferred embodiments thereof, given by way of example only with reference to the accompanying drawings.

BRIEF DESCRIPTION OF THE DRAWINGS

In the appended drawings:

FIG. 1 is a perspective view of a lancet according to a preferred embodiment of the present invention, illustrated in use;

FIG. 2 is a side elevational view of the lancet of FIG. 1 before use, where one of the half-shells has been removed;

FIG. 3 is a side elevational view similar to FIG. 2 illustrating the elongated body in its neutral safe position;

DESCRIPTION OF THE PREFERRED EMBODIMENT

Figure 5:
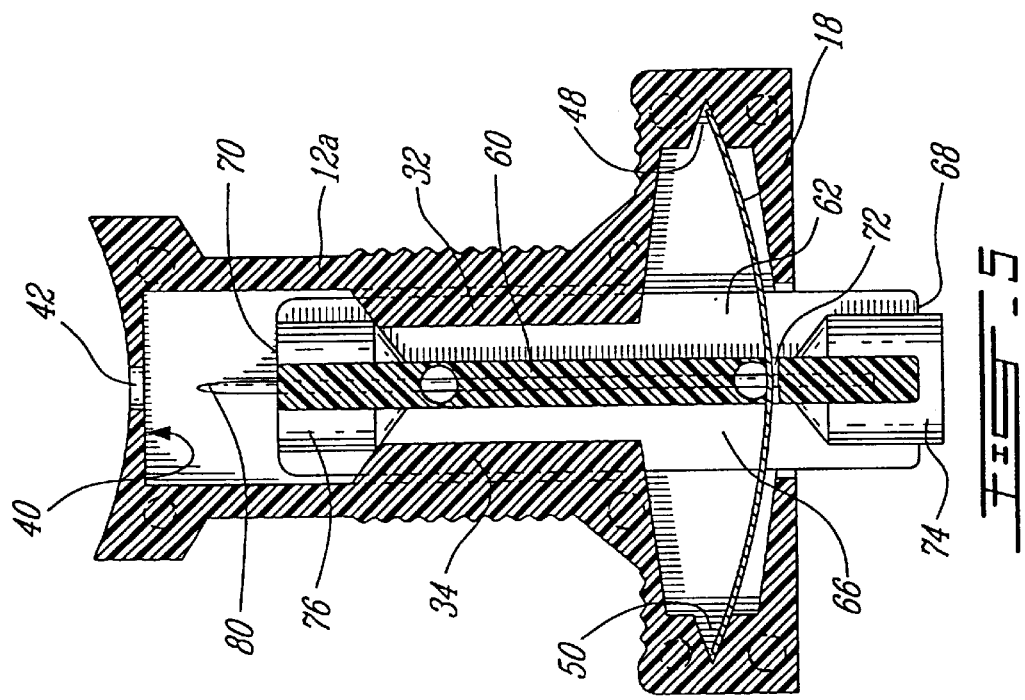
FIG. 5 is a sectional view taken along line 5—5 of FIG. 4.

Referring now to appended FIGS. 1 to 5, a disposable lancet 10, according to a preferred embodiment of the present invention, will be described.

The lancet 10 comprises a generally T-shaped housing 12, an elongated body 14 that embeds a puncturing device in the form of a needle 16, and a leaf spring 18.

Figure 4:
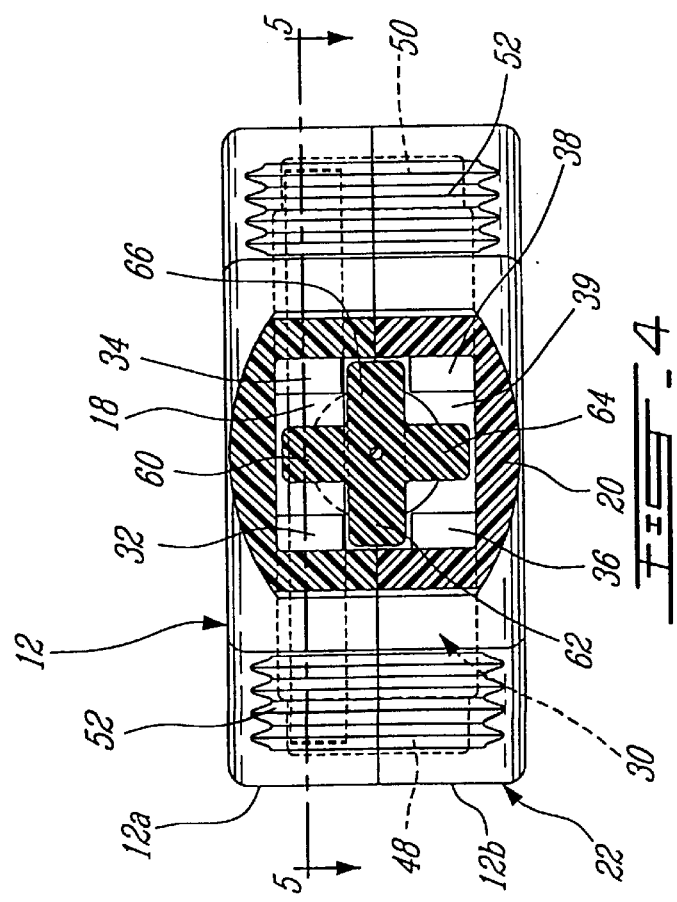
FIG. 4 is a sectional view taken along line 4—4 of FIG. 2.

The T-shaped housing 12 is made of two identical half-shells 12a, 12b (see FIG. 4). Since the half-shells 12a and 12b are identical, only half shell 12a will be described hereinbelow. Half-shell 12a includes an elongated portion 20 and a handle portion 22. The elongated portion 20 defines a passage 24 having a proximal end 26 and a distal end 28. The handle portion 22 defines a recess 30 that intersects generally perpendicularly to the passage 24 near the proximal end 26 thereof.

The passage 24 includes four protrusions 32–38 (see for example FIG. 4) that create a generally cross-shaped section 39 in a portion of the passage 24.

The distal end 28 of the passage 24 is closed by a wall 40 provided with a small aperture 42 centered therein. As will be explained in more detail hereinbelow, the aperture 42 is configured and sized to allow passage of the needle 16, while the wall 40 limits the projection of the needle 16.

The recess 30 is configured and sized to receive the leaf spring 18. More precisely, the recess 30 has a gradually decreasing height from its center to its opposite ends to accommodate the movements of the leaf spring 18. The decreasing height is defined by a first and a second opposite generally angled walls 44 and 46. Each of the two walls 44 and 46 includes a generally cross-shaped aperture to allow the insertion of the elongated body 14 therein. The cross-shaped aperture in the second angled wall 46 also corresponds to the proximal end 26 of the passage 24. Each lateral end of the recess 30 includes a V-shaped groove 48, 50 for receiving the longitudinal ends of the leaf spring 18. The V-shaped grooves 48, 50 extends outwardly with respect to the passage 24. It is to be noted that the recess 30 is so sized as to provide a distance between the two V-shaped grooves 48 and 50 smaller then the compressed length of the leaf spring 18 so as to ensure that the leaf spring 18 is bent.

The outside surface of the T-shaped housing 12 is advantageously provided with friction generating surfaces, in the form of ridges 52 and 54, respectively provided on the handle portion 22 and on the elongated portion 20.

The distal end 28 of the elongated portion 20 is advantageously provided with an external contacting surface 58 configured and sized to contour a finger.

As can be better seen from FIG. 4, the elongated body 14 comprises four perpendicular fins 60–66 extending longitudinally from a proximal end 68 to a distal end 70 of the body 14. The four perpendicular fins 60–66 define a generally cross-shaped cross-section and are configured and sized to guide the elongated body 14 in the cross-shaped section of the passage 24 defined by the four protrusions 32–38. The four fins 60–66 and the cross-shaped section of the passage 24 advantageously bring stability to the elongated body 14 while it reciprocally moves in the housing 12.

Fin 64 is provided with a transversal notch 72, near the proximal end 68 of the elongated body 14, to receive the leaf spring 18.

The elongated body 14 also includes two cylindrical portions 74 and 76, embedded in the four perpendicular fins 60–66 at the proximal and distal ends 68 and 70.

The needle 16 is centrally embedded in the elongated body 14 and extends outwardly from the distal end 70 thereof. The needle 16 advantageously includes a tri-beveled (not shown) point 80.

The lancet 10 is advantageously provided with a cap 78, integrally mounted to the distal end 70 of the elongated body 14, to cover the point 80 of the needle 16 before the lancet is used.

The elongated body 14 is preferably made of a neutral non corrosive and mouldable material, such as, for example, plastic, that is moulded around the needle 16. The cap 78 is advantageously moulded integrally with the elongated body 14. It is to be noted that the needle point 80 is sterilized subsequent to its covering by the cap 78, using, for example, gamma radiation.

The elongated body 14, with the cap 78 and needle 16 form an assembly similar to the Vitalet™ lancet model numbers P1511 and P1515, from the P1500 series, manufactured by *Medical Plastic Devices Inc.*

The two identical half-shells defining the housing 12 are provided with cooperating buttons and holes 86 conventionally used to assemble the two half-shells.

The leaf spring 18 is positioned in the V-shaped notches 48, 50 of the recess 30. The angle of these V-notches is sufficient to allow the two opposite positions of the leaf spring 18 as seen on FIGS. 2 and 3. The leaf spring 18 is made of a resilient material, such as for example stainless steel. The initial shape of the leaf spring 18 is illustrated in FIG. 3.

The two half-shells T-shaped housing 12 allows the lancet 10 to be easily assembled as follows:

the leaf spring 18 is first inserted in the V-shaped notches 48, 50 of the recess 30 of one of the two half-shells 12a, 12b of the housing 12; the leaf spring 18 is so positioned that its natural convex surface faces the proximal end 26 of the passage 24;

the elongated body 14, with the cap 78, is then so positioned in the passage 24 that its distal end 70 abuts the wall 40 while the leaf spring 18 is inserted in the transversal notch 72; the integral cap 78 is then positioned outside the housing and the leaf spring 18 is stressed as illustrated in FIG. 2;

the other half-shell of the T-shaped housing 12 is mounted to the first part.

The operation of the lancet 10 will now be described in more detail.

The first step is to remove the cap 78 by twisting it off. Since the link between the elongated body 14 and the cap 78 is relatively weak, the removal of the cap 78 is relatively easy.

Without the cap 78 to hold the distal end 70 of the elongated body 14 against the wall 40, the leaf spring 18 biases the elongated body 14 towards a neutral safe position, where a) the point 80 of the needle 16 is completely retracted in the housing 12 and b) the cylindrical portion 74 extends from the housing 12. The neutral safe position is illustrated in FIG. 3.

The lancet 10 is then held between two fingers 88–90, as illustrated in FIG. 1, with the thumb 92 ready to depress the cylindrical portion 74 of the elongated body 14.

The contacting surface 58 of the elongated portion 20 of the housing 12 is positioned on a finger 94 to be punctured.

The elongated body 14 is then moved from its neutral position to a puncturing position by depressing the cylindrical portion 74 of the elongated body 14. The depressing force must obviously be sufficient to overcome the biasing action of the leaf spring 18. The movement of the elongated body 14 is stopped when the distal end 70 of the elongated body reaches the wall 40. It is to be noted that the point 80 of the needle 16 is inserted in the finger 94 when the movement of the elongated body 14 is stopped by the wall 40.

When pressure is removed from the cylindrical portion 74, the elongated body 14 returns to its neutral safe position under the biasing action of the leaf spring 18.

Although the lancet according to the present invention has been described puncturing a finger, it can also be used to puncture other body parts, such as for example, an ear lob.

It is to be noted that the elongated body 14 can be made from more than one part without departing from the spirit of the present invention.

It is also to be noted that the T-shaped housing 12, the grooves 52 and 54 and the contacting surface 58 are provided to improve the ease of use of the lancet 10 and to provide a more safe use thereof.

Finally, it is believed within the reach of someone skilled in the art, to position the leaf spring 18 differently in the housing so as to provide the same biasing action on the elongated body 14.

Although the present invention has been described hereinabove by way of preferred embodiments thereof, it can be modified, without departing from the spirit and nature of the subject invention as defined in the appended claims.

What is claimed is:

1. A lancet for puncturing skin, said lancet comprising:
   a housing defining a passage having a proximal end and a distal end;

said housing including a recess;

an elongated body having a proximal end and a distal end;

said elongated body being so mounted in said passage as to reciprocate between a safe neutral position and a puncturing position and as to prevent its removal therefrom;

a puncturing device provided at said distal end of said elongated body;

said puncturing device extending from said distal end of said passage when said elongated body is in said puncturing position; and a leaf spring received in said recess and being so removably mounted to said elongated body as to bias said elongated body towards said safe neutral position;

wherein said elongated body is moved from said safe neutral position to said puncturing position when a force is so applied thereto as to overcome the biasing action of said leaf spring.

2. A lancet as recited in claim 1, wherein said housing includes two identical half-shells.

3. A lancet as recited in claim 1, wherein said housing includes a handle portion.

4. A lancet as recited in claim 3, wherein said housing is generally T-shaped.

5. A lancet as recited in claim 1, wherein the exterior surface of said housing includes friction generating surfaces.

6. A lancet as recited in claim 1, wherein said housing includes an end wall to limit the movement of said elongated body in said passage.

7. A lancet as recited in claim 1, wherein said housing includes an elongated portion having a proximate end and a distal end and defining a passage therein.

8. A lancet as recited in claim 7, wherein said distal end of said elongated portion includes an external contacting surface to contour a body part.

9. A lancet as recited in claim 1, wherein a) said elongated body has a generally cross-shaped cross-section, and b) said passage includes a corresponding cross-shaped portion to guide said elongated body.

10. A lancet as recited in claim 1, wherein said elongated body includes at least one fin to guide said elongated body in said passage.

11. A lancet as recited in claim 1, wherein said elongated body includes a transversal notch configured and sized to receive a portion of said leaf spring.

12. A lancet as recited in claim 1, wherein said recess includes two opposite angled walls.

13. A lancet as recited in claim 1, wherein said recess includes opposite V-shaped notches configured and sized to receive opposite ends of the leaf spring.

14. A lancet as recited in claim 1, wherein said puncturing device is a needle.

15. A lancet as recited in claim 14, wherein said needle includes a bevelled point.

16. A lancet as recited in claim 14, wherein said needle includes a tri-bevelled point.

17. A lancet as recited in claim 1, wherein said puncturing device is embedded in said elongated body.

18. A lancet as recited in claim 1, further comprising a removable cap to cover the puncturing device.

19. A lancet as recited in claim 18, wherein said removable cap is integrally mounted to said distal end of said elongated body.

20. A lancet for puncturing skin, said lancet comprising:

a housing defining a passage having a proximal end and a distal end;

said housing including a recess;

an elongated body having a proximal end and a distal end;

said elongated body being so mounted in said passage as to reciprocate between a safe neutral position and a puncturing position and as to prevent its removal therefrom;

a puncturing device provided at said distal end of said elongated body;

said puncturing device extending from said distal end of said passage when said elongated body is in said puncturing position; and a single leaf spring completely received in said recess and being so mounted to said elongated body as to bias said elongated body towards said safe neutral position and as to force with a snap action said elongated body towards said puncturing position when a predetermined force is applied as to overcome the biasing action of said leaf spring.

* * * * *